United States Patent [19]
Rydell

[11] Patent Number: 5,098,431
[45] Date of Patent: Mar. 24, 1992

[54] RF ABLATION CATHETER

[75] Inventor: Mark A. Rydell, Golden Valley, Minn.

[73] Assignee: Everest Medical Corporation, Minneapolis, Minn.

[21] Appl. No.: 547,765

[22] Filed: Jul. 3, 1990

Related U.S. Application Data

[63] Continuation-in-part of Ser. No. 337,428, Apr. 13, 1989, abandoned.

[51] Int. Cl.⁵ .............................................. A61B 17/39
[52] U.S. Cl. .................................................... 606/48
[58] Field of Search ................... 606/33, 41, 45, 46, 606/48, 50; 128/786

[56] References Cited

U.S. PATENT DOCUMENTS

| | | |
|---|---|---|
| 164,184 | 6/1875 | Kidder . |
| 3,460,539 | 8/1969 | Anhalt . |
| 3,595,239 | 7/1971 | Peterson . |
| 4,011,872 | 3/1977 | Komiya . |
| 4,228,800 | 10/1980 | Degler . |
| 4,532,924 | 8/1985 | Auth et al. . |
| 4,641,649 | 2/1987 | Walinsky ........................ 606/33 |
| 4,654,024 | 3/1987 | Crittenden et al. . |
| 4,682,596 | 7/1987 | Bales et al. . |
| 4,706,667 | 11/1987 | Roos . |
| 4,765,331 | 8/1988 | Petruzzi et al. . |
| 4,936,281 | 6/1990 | Stasz ........................ 606/48 X |
| 4,976,711 | 12/1990 | Parins et al. ........................ 606/48 |

Primary Examiner—Lee S. Cohen
Attorney, Agent, or Firm—Haugen and Nikolai

[57] ABSTRACT

An intravascular catheter especially designed to surgically remove atheromas or other forms of stenotic or thrombotic lesions from the interior walls of a blood vessel using an RF discharge between two bipolar electrodes is described. Affixed to the distal end of an elongated, flexible, plastic, tubular member is a bipolar electrode structure comprising a cylindrical insulator having a first conductive metal ring electrode surrounding the periphery of that insulator. Projecting from the distal end of the cylindrical insulator is a second, frusto-conical shaped member whose major base is slightly less in diameter than the diameter of the cylindrical insulator. An insulative material covers all but the distal side edge of the first ring electrode and an annular zone of the second electrode located immediately adjacent to the exposed distal side edge of the first electrode. Wires running through the lumen of the tubular member couple the first and second electrodes to an RF generator coupled to the catheters's proximal end. When appropriately energized, an intense current flow path is created between the exposed electrode surfaces for cutting through the blood vessel obstruction. The cone shaped member is rotatable about an axis which is eccentric to the centerline of the cylindrical insulator and by manually manipulating a torquing wire or tube at its proximal end, the electrode gap can be varied to control the location where cutting occurs. A motor device may also be used to continuously rotate the torquing wire.

12 Claims, 1 Drawing Sheet

RF ABLATION CATHETER

CROSS-REFERENCE TO RELATED APPLICATION

This application is a continuation-in-part in application Ser. No. 07/337,428, filed Apr. 13, 1989, and entitled "RF ABLATION CATHETER", now abandoned.

BACKGROUND OF THE INVENTION

I. Field of the Invention

This invention relates generally to an electrosurgical device for removing unwanted tissue and more particularly to an intravascular catheter having bipolar electrodes at the distal end thereof across which a high intensity RF current can be made to flow for cutting away atheromas or other lesions which may be partially occluding a blood vessel.

II. Discussion of the Prior Art

The buildup of atheromas or the formation of thrombi in a blood vessel can cause serious circulatory problems and when complete blockage occurs, distal tissues may be deprived of oxygen and nutrients, leading to damage or destruction of cell tissue distally of the blockage. As the blockage grows, distal tissue may become more ischemic unless, of course, channelization occurs whereby blood bypasses the constriction. With a narrowed blood vessel, a point may be reached where even a tiny thrombus becomes lodged creating an infarct.

The treatment of diseased blood vessels depends to a large extent on the location of the blockage. In the case of a blocked or partially blocked coronary artery, it has been the practice to perform coronary bypass surgery. In a like fashion, blood vessel shunts have been installed in other body areas as well. The surgery involved in those procedures tends to be quite traumatic, involving, in the case of coronary-bypass surgery, the opening of the patient's chest and pericardium. In treating deep vein thrombosis or other blockages in the peripheral vasculature, extensive excision and vessel replacement is often required.

More recently, following the technique credited to A. Grunzig, a balloon catheter has been used to restore patency to blood vessels without extensive surgery. In carrying out this technique, a catheter having a small inflatable balloon on its distal end is routed through the vascular system to the site of the restriction to be treated. The deflated balloon is appropriately positioned to span the blockage in question and then a fluid is introduced into the proximal end of the catheter to inflate the balloon to a sufficiently high pressure whereby the blockage is spread open and patency is restored.

As is pointed out in the U.S. Pat. No. 4,445,509 to Auth, there are some deficiencies in the Grunzig procedure which renders it ineffective in certain applications. For example, the blockage may be such that it is not possible to safely force the distal tip of the catheter through the blockage prior to the inflation of the balloon. The Auth patent also cites a number of other U.S. patents relating to catheter-mounted cutting devices intended to "tunnel" through a blockage but without doing damage to the healthy blood vessel tissue. The invention of the Auth patent is in the design of a rotatably driven cutting tool which will preferentially abrade hard or calcified lesions while not significantly abrading the endothelial lining of the blood vessel.

Atherectomy catheters with rotary cutting heads are difficult and costly to make, especially given the need for providing seals on shafts moving at very high speeds. The RF ablation catheter of the present invention is substantially easier to produce in that no moving parts are involved. Also, the debris released downstream from rotating cutters may be substantial, whereas debris from RF ablation is very small and more easily tolerated by the body.

SUMMARY OF THE INVENTION

In accordance with the present invention, there is provided an RF ablation catheter especially designed for removing stenotic lesions from seriously blocked blood vessels. The device comprises an elongated, plastic, flexible, tubular member which is dimensioned so as to pass through a guide catheter to the site of the lesion to be treated. Disposed on the distal end of the catheter body is a tip member which includes first and second spaced electrodes, with the tip member being configured to produce a general centering thereof within the blood vessel being treated. In this regard, it has been found convenient to provide as the most proximal electrode an electrically conductive annular ring surface lying in a transverse plane and as the most distal electrode a conic frustum which tapers in the distal direction from a larger diameter at its major base to a lesser diameter at its minor base. The cone portion is disposed eccentrically relative to the center of the annular proximal electrode and is rotatable about a longitudinal axis by manipulating a knob at the proximal end of the catheter body. As such the gap between the electrodes can be adjusted. A set of wires run the full length of the catheter body so that an appropriate RF voltage can be impressed across the electrodes to generate a high intensity current, e.g. an arc discharge, at a radial location which can be shifted by rotation of the cone portion. When the stenotic tissue is exposed to the high intensity current path, it electrosurgically cuts away the tissue comprising the blockage. Because of the design of the distal tip member, the arc can be preferentially directed, thereby avoiding damage to healthy blood vessel tissue.

DESCRIPTION OF THE PREFERRED EMBODIMENT

Figure 1:
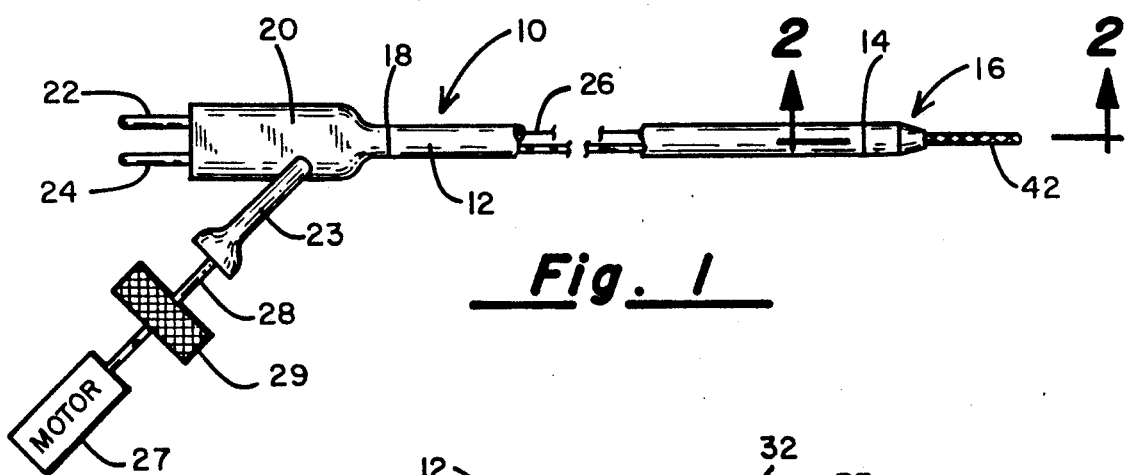
FIG. 1 is a side elevation of a electrosurgical catheter in accordance with the present invention.

Referring first to FIG. 1 there is indicated generally by numeral 10 an ablation catheter constructed in accordance with the present invention. It is seen to include an elongated tubular body 12, which is preferably formed from a suitable, medical-grade plastic and dimensioned such that it may be introduced at a predetermined location in a living body and routed through the vascular system, all in accordance with known catheterization procedures. Affixed to the distal end 14 of the tubular body 12 is a tip member 16, the construction details of which are set out hereinafter. Appropriately bonded to the proximal end 18 of the tubular body 12 is an electrical connector 20 having a pair of terminals 22 and 24 which can be plugged into a suitable RF voltage generator and a side entry port 23. The terminals 22 and 24 are joined by suitable means to electrical conductors 26 and 28 which extend through the lumen of the tubular body 12 to separate, spaced-apart electrodes on the tip member 16. Conductor 28 is preferably a long, flexible rod, wire or tube which passes into the port 23 and includes a knob 29 to facilitate its rotation.

Figure 2:
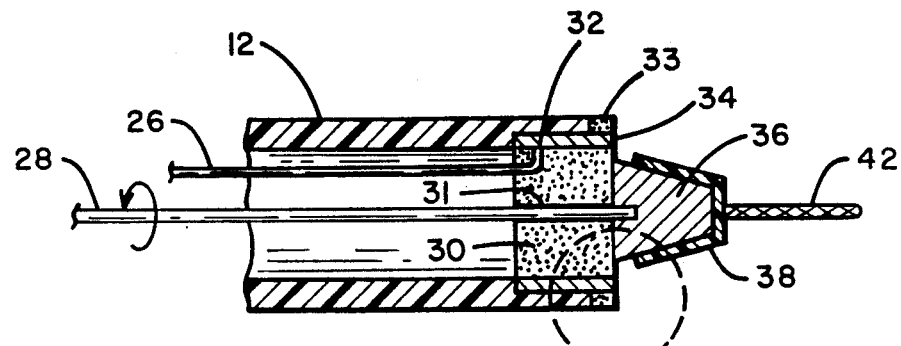
FIG. 2 is a greatly enlarged cross-sectional view taken along the lines 2—2 in FIG. 1.

With reference to the cross-sectional view of FIG. 2, the tip member 16 is seen to comprise a right circular cylinder 30 which is preferably formed from a ceramic or other non-conductive material capable of withstanding the high operating temperatures encountered. Surrounding the cylindrical ceramic core 30 is a metal annulus 32 to which the conductor 26 is shown as being electrically connected. The plastic tube 12 extends over a substantial portion of the surface of conductive ring 32 with the remaining distally located portion being covered with a plasma sprayed ceramic 33 capable of withstanding the temperatures proximate the effective electrode surface. Thus, the effective electrode surface, i.e., the uninsulated surface, of the conductive ring 32 is a circular band 34 whose thickness preferably lies in the range of from 0.003 to 0.010 inches.

Figure 3:
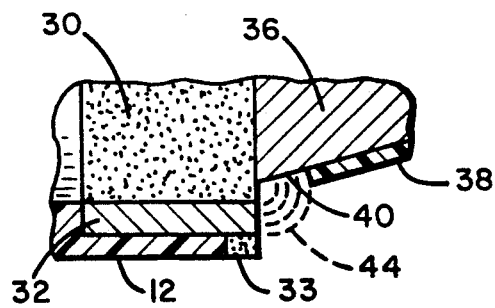
FIG. 3 is a further enlargement of the electrosurgical cutting tip showing the location of the arc discharge.

Mounted for rotation on the transverse distal edge of the ceramic cylinder 30 is an electrically conductive body 36 of a frusto-conical shape, the major base abutting the distal side surface of the ceramic cylinder 30. The wire or rod 28 passes through a centrally located bore 31 in the member 30 and is conductively fastened to the body 36 at a location offset from its central access by a small eccentricity. As shown in FIGS. 2 and 3, a majority of the surface of the frusto-conical shaped conductive body 36 is coated with an insulating plastic material such as Teflon layer 38 so that only a narrow band 40 comprising a second electrode surface remains uncovered. This band is immediately adjacent the transverse distal edge of the ceramic core 30 and is displaced from the electrode surface (band 34) of the metal ring 32 by a variable gap distance. That is, the diameter of the major base of the body 36 is less than the diameter of the ceramic member 30 and, accordingly, the band 40 comprising the second electrode is offset from the first electrode (ring 32) by a predetermined gap distance. By rotating the knob 29 and, hence, the body 36, the gap between the two electrodes may be made to vary between from about 0.003 inches as a minimum and to 0.020 inches as a maximum. It is also envisioned that the connecting wire 28 can be continuously torqued by employing a small, D.C. motor 27 either directly coupled or coupled through a gear reduction to drive the wire 28 at a low speed, e.g., 10–50 r.p.m. to cause the narrow point of the gap to sweep out a circular orbit at a fixed rate. A conventional slip ring connection (not shown) is made between the torque wire 28 and the input terminal 24, allowing it to rotate while also providing electrical continuity.

A short length of flexible guidewire 42 is preferably bonded to the minor base of the frusto-conical shaped electrode 36 and is also covered with a insulative coating, e.g., Teflon. The guidewire segment 42 facilitates the steering of the RF catheter into a desired vascular branch as the knob 29 is manipulated.

In operation, an electrosurgical RF generator, such as of the type disclosed in the U.S. Pat. No. 4,903,696, issued Feb. 27, 1990, and entitled ELECTROSURGICAL GENERATOR and assigned to applicant's assignee, may have its output coupled to the terminals 22 and 24 of the RF catheter 10. When energized, a RF voltage will be developed between the exposed electrode surfaces 34 and 40. The output of the RF generator may be adjusted so as to create a high intensity current flow path or even an arc discharge as indicated by the dashed arcuate lines 44 in FIG. 3.

As the catheter of the present invention is advanced against a stenotic lesion which is generally symmetrically formed on the blood vessel wall, the tapered conical shape of the member 36 will tend to center itself in whatever lumen may be present in the lesion. Now, when the RF energy is applied so as to create an arc discharge, the tissue abutting the annular ring will be cut, tunneling through the blockage. Because the location of the arc is precisely focused by including the insulative coverings thereon, only the material comprising the lesion will be effected by the RF cutting, thus leaving the healthy blood vessel tissue unaffected. In the event the lesion to be treated covers only a limited portion of a blood vessel, i.e., it is asymmetrical, the surgeon may, by manually rotating the knob 29, cause the electrode gap to be small in the area of the lesion, but large enough next to the normal vascular tissue to preclude cutting. If a motor is used to torque the wire 28, the high intensity current/arc used for cutting can be made to sweep in a circular orbit.

Figure 4:
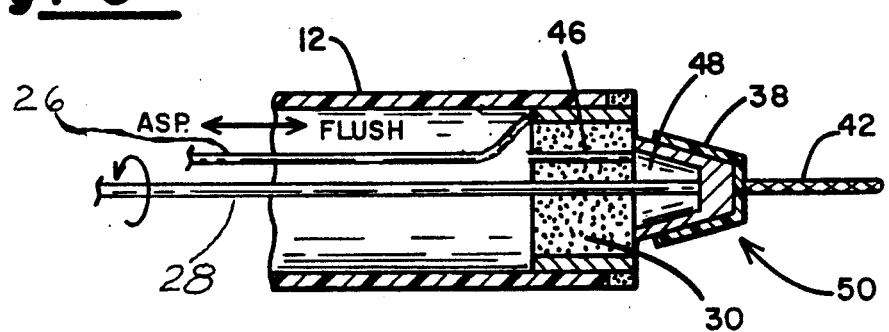
FIG. 4 is an enlarged cross-sectional view showing an alternative embodiment of the present invention.

FIG. 4 is another enlarged view of the tip member illustrating the manner in which either flushing or aspiration may be carried out during the procedure. The arrangement shown in FIG. 4 differs from that of FIG. 2 in that there is provided through the ceramic cylinder 30 a central bore 46 which is in fluid communication with a hollow 48 formed in the frusto-conical member 50. When a fluid is injected into the proximal end of the catheter, it perfuses out the interface space between ceramic member 30 and the frusto-conical tip portion 50. Alternatively, by coupling a vacuum source to the lumen of the tubular member 12 at its proximal end, the site at which the distal tip member is located can be aspirated. Hence, if during the course of an electrosurgical ablation of a vascular lesion, carbon particles or fulgurated blood and tissue particles can be drawn from the treatment site and through the catheter body.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An intravascular RF ablation catheter for removing stenotic lesions from a blood vessel, comprising:
   (a) an elongated, plastic, flexible tubular member having a proximal end, a distal end and a lumen extending therebetween;
   (b) first and second electrical conductors, each having a proximal end and a distal end, said conductors extending through said lumen;
   (c) a tip member attached to said distal end of said tubular member, said tip member including (i) a cylindrical insulating member surrounded by an annular first electrode, said insulating member and annular electrode being inset into said distal end of said tubular member with only an edge surface of said first electrode exposed at said distal end of said tubular member, (ii) a frusto-conical shaped electrically conductive second electrode having a major base and a minor base with said major base positioned adjacent said cylindrical insulating member and separated from said first electrode by an annular insulating gap; and (d) means for connecting said first electrode to said first conductor and said second electrode to said second conductor.

2. The RF ablation catheter as in claim 1 wherein said first electrode is fixed and said second electrode is rotatable relative to said first electrode.

3. The catheter as in claim 1 and further including an insulating sheath covering predetermined surfaces of said frusto-conical shaped conductive electrode.

4. The catheter as in claim 1 and further including a guidewire attached to said minor base of said frusto-conical shaped second electrode.

5. The catheter as in claim 1 and further including means for applying an RF electrical voltage between said first and second electrodes to produce a current flow sufficiently intense to cut through body tissue positioned across said annular gap.

6. An intravascular RF ablation catheter comprising:
(a) an elongated, flexible, plastic tubular body having a proximal end and a distal end and a lumen extending therebetween;
(b) an insulating cylindrical plug inset into said distal end of said tubular body;
(c) a first, annular electrode surrounding said plug;
(d) a second, conically-tapered electrode said second electrode being attached to said plug such that said second electrode is spaced from said first annular electrode by an annular gap; and
(e) conductor means extending the length of said body from said proximal end to said distal end for coupling a RF voltage to said first and second electrodes, said voltage being sufficient to effect cutting of tissue by an intense current flow across said gap.

7. The catheter as in claim 6 and further including insulating means masking portions of said first and second electrodes for defining the location of said intense current flow.

8. The catheter as in claim 6 and further including a fixed guidewire attached to said conically-tapered electrode.

9. The catheter as in claim 6 wherein said conically-tapered electrode is rotatably attached to said plug.

10. The catheter as in claim 6 wherein said conically-tapered electrode is eccentrically and rotatably attached to said plug.

11. The catheter as in claims 9 and 10 and further including means including one of said conductor means coupled to said proximal end of said tubular body for imparting rotation to said conically-tapered electrode.

12. The catheter as in claim 11 wherein said means for imparting rotation is a motor operatively coupled to said one of said conductor means.

* * * * *